US006159241A

United States Patent [19]
Lee et al.

[11] Patent Number: 6,159,241
[45] Date of Patent: Dec. 12, 2000

[54] METHOD AND APPARATUS FOR ADJUSTING CORNEAL CURVATURE USING MULTIPLE REMOVABLE CORNEAL IMPLANTS

[75] Inventors: Joseph Y. Lee, 1421 San Bernadino Rd., #39N, Upland, Calif. 91786; Stephen I. Jang, Redlands, Calif.

[73] Assignee: Joseph Y. Lee

[21] Appl. No.: 09/280,259

[22] Filed: Mar. 29, 1999

Related U.S. Application Data

[63] Continuation-in-part of application No. 08/829,846, Apr. 1, 1997, Pat. No. 5,855,604.
[60] Provisional application No. 60/079,930, Mar. 30, 1998.
[51] Int. Cl.$^7$ .................................................. A61F 2/14
[52] U.S. Cl. ............................................ 623/5.12; 623/5.11
[58] Field of Search ................................... 623/5.11, 5.12

[56] References Cited

U.S. PATENT DOCUMENTS 5,090,955  2/1992  Simon .
5,733,334  3/1998  Lee .

FOREIGN PATENT DOCUMENTS

WO 94/06504  3/1994  WIPO .

*Primary Examiner*—Dinh X. Nguyen
*Attorney, Agent, or Firm*—McCutchen, Doyle, Brown & Enersen, LLP

[57] ABSTRACT

Methods are disclosed for adjusting corneal curvature to correct the refractive error of an eye. The method comprises a first corrective event in which the corneal curvature is adjusted to correct the eye to 20/20 vision or slightly over-correct the eye past 20/20 vision. After the first corrective event, a second corrective event adjusts the corneal curvature to 20/20 vision. The second corrective event causes significantly less trauma to the eye, and thus, compared to the first corrective event, the error from healing and other factors is greatly reduced in this second corrective event. Devices for implementing these methods are also disclosed.

1 Claim, 13 Drawing Sheets

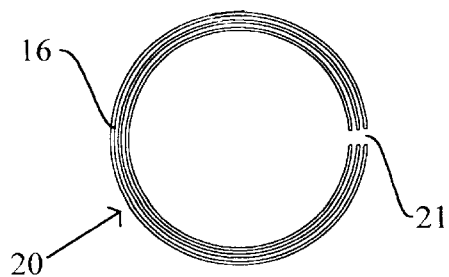
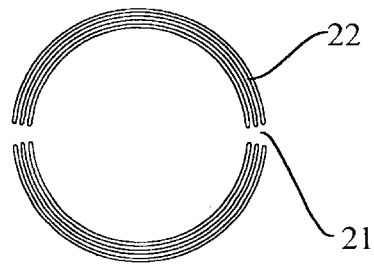
FIG. 4(a)        FIG. 4(b)
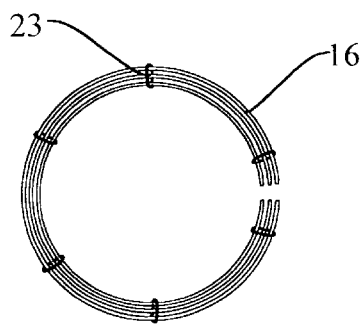
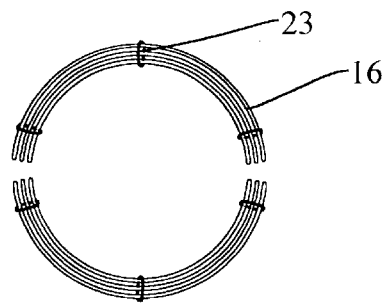
FIG. 5(a)        FIG. 5(b)
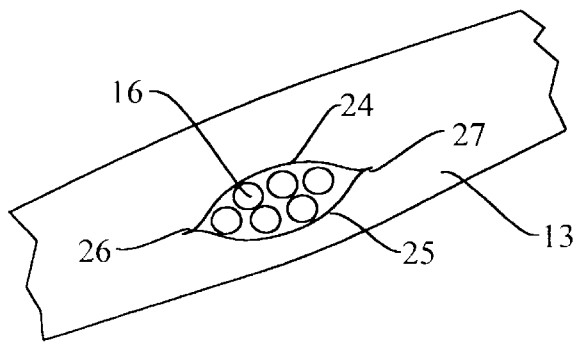
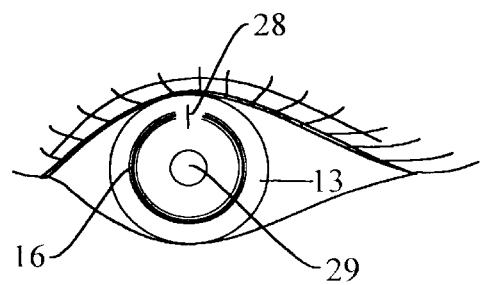
FIG. 6(a)        FIG. 6(b)

Distribution of Typical Refractive Surgery Outcomes

Expected Distribution of Refractive Surgery Outcomes with Hyperopic Over-Correction Expected Distribution of Refractive Surgery Outcome Following Partial Reversal (Adjustment) Procedure

METHOD AND APPARATUS FOR ADJUSTING CORNEAL CURVATURE USING MULTIPLE REMOVABLE CORNEAL IMPLANTS

CROSS-REFERENCE TO RELATED APPLICATIONS

This patent application claims 119(e) benefit of prior Provisional Application Ser. No. 60/079,930, filed Mar. 30, 1998, which provisional application is a continuation-in-part, of U.S. patent application Ser. No. 08/829,846, filed Apr. 1, 1997 now U.S. Pat. No. 5,855,604.

FIELD OF THE INVENTION

This invention relates to a method and apparatus for adjusting corneal curvature and, more particularly, to an implantable device adapted for insertion into the peripheral cornea of an eye and which may be modified in the amount of volume of peripheral corneal tissue it displaces at the time of insertion and at post-operative times to correct refractive error by removing solid material from the implanted device.

BACKGROUND OF THE INVENTION

Ametropia, an undesirable refractive condition of the eye, has three main subdivisions: myopia, hyperopia, and astigmatism. In myopia, by far the most common type of ametropia, the parallel light rays 1 which enter the eye as shown in FIG. 1(c) come to a focus F3 in front of the retina 2. In hyperopia, the rays of light 1 come to a focus F2 behind the retina 2 as shown in FIG. 1(b). When the rays of light converge to not one, but several foci, it is referred to as astigmatism, in which condition the various foci may all lie before the retina; all lie behind the retina; or partly before and partly behind the retina.

Ametropia is usually corrected by glasses or contact lenses. However, these refractive disorders may also be corrected by surgery. Refractive eye surgery is defined as that surgery on the eye that acts to change the light-bending qualities of the eye. More common current refractive procedures include radial keratotomy, as described in U.S. Pat. Nos. 4,815,463 and 4,688,570 and also laser ablation of corneal stroma, described in U.S. Pat. No. 4,941,093. Various other surgical methods for the correction of refractive disorders have been tried including thermokeratoplasty for the treatment of hyperopia, epikeratoplasty to correct severe hyperopia, and keratomnileusis, which can steepen or flatten the central cornea. Keratomileusis was introduced by Barraquer of Colombia in 1961 and essentially involves grinding a corneal button into an appropriate shape to correct the refractive error and replacing the reshaped corneal button. Some of the more commnon keratorefractive procedures are discussed below; none of which have all the characteristics of an ideal keratorefractive procedure. The disadvantages of corneal refractive surgery include limited predictability, lack of reversibility, corneal destabilization, optical zone fibrosis, post-operative discomfort, and visual symptoms such as glare, halos, and starbursts.

In radial keratotomy (RK), multiple peripheral radial incisions are made into the cornea at 90–95% depth in an attempt to flatten the central cornea and thus correct myopia. The problem of unpredictability of result was tackled by multiple extensive retrospective analyses of the patients in whom surgery had already been performed. These studies revealed certain factors that seemed to control the outcome of the surgery, such as the size of the optical zone, the initial keratometric readings, corneal diameter, corneal rigidity, number of incisions, incision depth, intra-ocular pressure, thickness of the cornea, and degree of astigmatism. Age and sex are also factors that are taken into consideration in most of the nomograms, which have been devised to predict what effect to expect for a certain surgery. At one point, many experts in the field considered it nearly impossible to fully and accurately correct patients in one surgery and felt that RK should be considered a two-stage surgery, with the initial surgery to achieve the "ball-park" correction, followed by an enhancement procedure to adjust or titrate the result near the desired outcome for an individual eye. It was felt that because of individual variability which may lead to an under or over-correction in the individual different from that predicted by the nomogram attempting to fully correct the refractive error in one surgery could lead to over-correction in a significant number of surgeries, resulting in hyperopia which is much more difficult to correct. Unfortunately, the second-stage surgery is even less predictable than the initial procedure. No one has yet devised a formula to take into account the profound changes which occur in the cornea after the initial RK, especially when weeks or months have passed. Most studies quote only 50–60% of eyes achieving 20/20 or better visual acuity following RK. Patients who are accustomed to 20/20 or better corrected visual acuity before surgery are not typically satisfied with less than 20/25 or 20/30 uncorrected post-operative visual acuity.

In addition, a gradual hyperopic shift is a major concern after RK. Refractive stability is critical for all refractive procedures but all corneal refractive procedures show significant degrees of instability. To date, there has been no clear explanation of why the cornea is destabilized by RK. A recent report on the long-term results of RK stressed the "natural" hyperopic refractive progression of "normal" eyes as a function of age. It is possible that patients are initially overcorrected and the over-correction masked by the patient's accommodative powers. With time and loss of accommodation, the hyperopia may be gradually unmasked with the hyperopia becoming visually symptomatic. At the time of surgery, a patient may be corrected with resultant slight hyperopia and yet have 20/20 vision because of the ability of the lens to accommodate. There is a range of residual correction within which the patient can have 20/20 uncorrected vision. This range varies depending on the individual but probably spans two to three diopters. Even with this range, the percentage achieving 20/20 is only 50–60%. This reflects poorly on the precision of the technique. It is important to note that this range diminishes with presbyopia, or loss of accommodation which usually begins at about 45 years of age. This results in the percentage achieving 20/20 dropping from the 50–60% described above. It is obvious that RK does not qualify as a simple, safe, predictable procedure to adjust the refractive outcome after the initial RK has been performed. Most ideas to contend with the corneal shape after this event have been purely empirical. Thus an easy method to fine-tune a refractive correction that is minimally invasive and easily performed would require serious consideration.

Laser stromal ablation procedures, such as photorefractive keratectomy (PRK) for correction of refractive disorders are currently popular and have had reasonable success. These procedures are not, however, spared from the problem of unpredictability. Essentially, in the treatment of myopia, laser energy is imparted to the central cornea thereby causing excision of more tissue centrally and a resultant flattening of the cornea. Unfortunately, the final refractive effect is determined not only by the amount of ablation but also by the healing response to the keratectomy. The cornea actively lays down new collagen and the epithelium undergoes a hyperplastic response, among other responses, in an attempt to repair the damage to its surface. This causes regression, or a shift backwards towards myopia, which can gradually occur over a period of months to years. An undesired effect of new collagen deposition is stromal scar formation which manifests as stromal haze and possible decrease in contrast sensitivity by the patient. This corneal stromal opacification is variously referred to as fibrosis, scarring, or haze which is associated with reduced visual acuity and contrast sensitivity, regression of the refractive effect, and poor night vision. Predictability with PRK is an issue, as with RK. Most published results of outcome after PRK treatment for myopia show 80–94% of eyes obtaining uncorrected visual acuity of 20/40 or better while the percentage of patients achieving 20/20 is significantly less. These numbers are in spite of the fact that there is a range of residual refraction at which the patient can still see 20/20 as previously explained. It can be assumed that a significant proportion of those achieving 20/20 after PRK are actually slightly hyperopic. It may very well be that with time, a significant percentage of those patients develop "progressive hyperopia", or an unmasking of the latent hyperopia. So, although the percentage of patients achieving 20/20 after PRK is not acceptable by the definition of an ideal refractive procedure, it may be inflated as was the initial results with RK. Although visual recovery is slow in RK, it is quicker than after PRK. A second laser ablation procedure is usually undertaken with caution since it may cause a greater healing response with even more regression than the initial procedure. Again, as in RK, the laser ablation procedure is not completely predictable, partly because one cannot predict an individual's wound healing response.

The criteria for an ideal refractive procedure include adjustability, predictability/efficacy, maintenance of quality of vision, reversibility, simplicity, stability, safety, and low cost. Each of these factors are reviewed:

1. Adjustability. Because of corneal wound healing and the delicate corneal curvature changes required to achieve 20/20 uncorrected vision, it is unlikely that any refractive procedure will achieve 20/20 vision with a single procedure. The refractive literature is abundant with comments and opinions describing the need for an adjustable procedure. PRK attempts adjustments or "enhancements by repeating the same process—removal of epithelium and re-ablation. If there was variability in the initial PRK procedure, it is unlikely that the same procedure will be able to "fine-tune" the refractive outcome.
2. Predictability/Efficacy. The bottom line is that only about 71% to 97% of eyes with baseline refractions less than or equal to 6 D achieve manifest post-op refractions within +/−1 D of the attempted correction one year after surgery. PRK, RK, and corneal ring literature all report similar efficacy data.
3. Quality of vision. PRK ablates the central cornea and corneal haze is an issue as evidenced by a small percentage of patients with a decrease in best-corrected visual acuity. Visually comprising complications include haze and scarring, halo effect, decreased contrast sensitivity, and decentration of ablation. Any procedure that operates on the central cornea will result in decreasing the best-corrected visual acuity in at least a small percentage of patients.
4. Reversibility. Many prominent refractive surgeons believe that the trend in refractive surgery would e towards reversible procedures. A reversible procedure, such as corneal rings, may likely be the procedure of choice for lower myopia and a reversible procedure, such as implantable intraocular lenses, may be the procedure of choice for higher myopia. Many potential patients have not had vision correction surgery because of its irreversibility.
5. Simplicity. A refractive procedure that only a few skilled refractive surgeons can perform will unlikely become a popular procedure. Also, difficult procedures typically have variable outcomes and a steeper learning curve. The complication rate for beginning refractive surgeons for a difficult procedure cannot be dismissed since there will always be new surgeons learning the procedure.
6. Stability. A long term complication of Radial Keratotomy is progressive hyperopia. PRK undergoes regression of effect.
7. Safety. Refractive surgeries are elective procedures and much of the initial resistance to performing these procedures in the late 80's was the philosophy among ophthalmologists that surgically manipulating a healthy eye with the potential for disastrous loss of vision was ethically unacceptable. PRK can cause central corneal haze sufficient to decrease best-corrected visual acuity. LASIK invades a central cornea with a microkeratome and is associated with multiple potential complications including lost flaps, button-holed flaps, free caps, thin flaps, and even perforation with extrusion of intraocular contents. In general, a corneal procedure is probably safer than an intraocular procedure and a peripheral corneal procedure safer than a central corneal procedure.

For well over a century, ophthalmologists have searched for a surgical method to permanently correct refractive errors. At least 15 different techniques have been developed and considerable experience has accumulated in both animal and human models. Laser photorefractive keratectomy has come the closest to gaining widespread acceptance in the ophthalmic community, but the difficulty in gaining acceptance for keratorefractive procedures is because of the unsolved problems with poorly predictable and unstable refractive outcomes, adverse effects on the quality of vision, lack of adjustability, and irreversibility.

Poor predictability looms as the largest unsolved problem with refractive corneal surgery. The two major factors that contribute to poor predictability are (a) the variability and inaccuracy inherent with manual surgical techniques, and (b) the variable influence of corneal wound healing in determining the refractive outcome. Until these two deficiencies are corrected, it is unlikely that a refractive surgical procedure will predictably correct ametropia to within a half diopter, the margin that can be achieved routinely with glasses or contact lenses.

Photorefractive keratectomy offers the possibility of solving one of the major causes of poor predictability by reducing the surgical variability of the procedure. A major unresolved issue is how the second nemesis that causes poor predictability, corneal wound healing, will affect the results of PRK. However, patients typically undergo regression of effect of approximately 1.0–1.5 diopters over six months. 9%–20% of patients continued to show myopic regression of 1 D or more even during the second year after surgery. There are "under-responders" who do not undergo any regression and there are over-responders who undergo up to 3 diopters of regression. So, although it is true that the excimer laser is precise to sub-micron accuracy, the variability in regression removes that advantage.

Typical refractive surgery studies, including RK and PRK, report the post-operative refraction in terms of the percentage of patients achieving +/−1 diopter of emmetropia. Approximately 80–90% of patients achieve this range. However, only approximately 50–60% of patients achieve uncorrected visual acuity of 20/20 without symptoms. The unsolved problem in refractive surgery is that only about half of patients achieve a vision of 20/20 without correction following current refractive procedures.

The goal in refractive surgery is to achieve emmetropia. However, there is a range of residual refractive error at which the patient can see 20/20 without correction. On the myopic side, a patient can be −0.30 D or less and still see 20/20 uncorrected. The issue is slightly more complex on the hyperopic side due to the availability of lens accommodation. The average 30 year-old has a total of 7 diopters of accommodation available to him and can easily supply several diopters from his "storehouse" of reserve. Reading a book or newspaper at arms-length (40 cm) requires 2.5 diopters of accommodation for the emmetrope. This means that a 30 year old patient may be overcorrected by up to 2.5 diopters and still see 20/20 uncorrected when tested, with minimal symptoms for distance vision since he is using only 2.5 diopters of the 7 D available to him. Of course, now to read, he will require 5.0 diopters of accommodation and will most likely be unable to read comfortably. In the ages of 35–40, the 1.50 diopter hyperope who could always get along easily without wearing his correction for distance vision will suddenly find that he cannot.

The modem refractive surgeon has several weapons in his armamentarium to choose from in attacking myopia. The refractive surgeon knows the limitations of his options. It is understood that RK is moderately predictable, adjustable only towards hyperopia, and irreversible. PRK is also moderately predictable, adjustable only towards hyperopia with the caveat that there is some regression towards myopia, but also essentially irreversible. On cardinal rule of refractive surgery is to avoid overcorrection because the options for a patient who is over-corrected to hyperopia are much more limited.

The dilemma results from the surgeon (and patient) wishing to achieve an uncorrected visual acuity of 20/20. The uncorrected visual acuity is poor if the post-op refraction is myopic but 20/20 if the post-op refraction is hyperopic. However, residual myopia can be "enhanced" while residual hyperopia is much more difficult to surgically manage.

This is best illustrated in a study comparing Summit and Visx lasers. The results showed a median refraction of 0.0 D in the Summit group and −0.5 D in the Visx group. The uncorrected visual acuity was 20/40 or better for 100% of the Summit treated eyes, whereas only 85% of the Visx treated eyes achieved 20/40 or better. Overcorrection results in a higher percentage of patients achieving 20/40 or better but results in a higher percentage of patients who are hyperopic. In other words, the higher percentage of patients achieving 20/40 in the Summit group may be explained by the accommodative reserve still present in the younger patients that were overcorrected.

For years it has been thought that refractive surgery with intracorneal implants could be used in the correction of ametropia. Early techniques included lamellar removal or addition of natural corneal stromal tissue, as in keratomileusis and keratophakia. These required the use of a microkeratome to remove a portion of the cornea followed by lathing of either the patient's (keratomileusis) or donor's (keratophakia) removed cornea. The equipment is complex, the surgical techniques difficult, and most disappointingly, the results quite variable. The current trend in keratorefractive surgery has been toward techniques that are less traumatic to the cornea, that minimally stimulate the wound healing response, and behave in a more predictable fashion. The use of alloplastic intracorneal lenses to correct the refractive state of the eye, first proposed in 1949 by Jose Barraquer, have been plagued with problems of biocompatibility, permeability to nutrients and oxygen, corneal and lens hydration status, etc. Other problems with these lenses included surgical manipulation of the central visual axis with the concomitant possibility of interface scarring.

More recent efforts toward the correction of refractive errors have focused on minimizing the effects of the wound healing response by avoiding the central cornea. There have been multiple attempts to alter the central corneal curvature by surgically manipulating the peripheral cornea. These techniques are discussed because of their specific relevance to this invention.

Zhivotovskii, D. S., USSR Patent No. 3,887,846, describes an alloplastic, flat, geometrically regular, annular ring for intracorneal implantation of an inside diameter that does not exceed the diameter of the pupil. Refractive correction is accomplished primarily by making the radius of curvature of the surface of the ring larger than the radius of curvature of the surface of a recipient's cornea in order to achieve flattening of the central area of the cornea. Surgical procedures for inserting the ring are not described.

A. B. Reynolds (U.S. Pat. No. 4,452,235) describes and claims a keratorefractive technique involving a method and apparatus for changing the shape of the optical zone of the cornea to correct refractive error. His method comprises inserting one end of a split ring shaped dissecting member into the stroma of the cornea, moving the member in an arcuate path around the cornea, releasably attaching one end of a split ring shaped adjusting member to one end of the dissecting member, reversibly moving the dissecting member about the path, and thereby pulling the adjusting member about the circular path, made by the dissecting member, withdrawing the dissecting member, adjusting the ends of the split-ring shaped adjusting member relative to one another to thereby adjust the ring diameter to change the diameter and shape of the cornea and fixedly attaching the ring's ends by gluing to maintain the desired topographical shape of the cornea.

A major advantage of this ring was that a very minimal wound healing effect was expected. A marked corneal wound healing response would decrease the long-term stability of any surgical refractive procedure. However, there are two distinct problem areas affecting the refractive outcome of surgical procedures treating ametropia:

1. The first problem is concerned with the ability to predetermine the shape and size of an implant that will lead to a certain refractive outcome. In RK or PRK, retrospective studies have been performed that led to the development of nomograms which predict that a certain depth cut or a certain ablation amount will result in a predictable amount of correction. In the case of the ring, eventually nomograms will be developed that can be used to predict a given refractive correction for a given thickness or size of the ring. However, these nomograms can never fully account for individual variability in the response to a given keratorefractive procedure.

2. The refractive outcome also depends on the stability of the refractive correction achieved after surgery. To reiterate, the advantage of the ring would be the stability of the refractive outcome achieved because of a presumed minimal wound healing response. This decreases the variability of the long-term refractive outcome but still does not address the problems posed in the first problem area, —the inherent individual variability, in that while the outcome may be stable, it may very well be an inadequate refractive outcome that is stable.

Another unaddressed issue is that even with the implant, surgeons will aim for a slight under-correction of myopia because, in general, patients are more unhappy with an overcorrection that results in hyperopia. Again, the refractive outcome may be more stable than in RK or PRK but it may be an insufficient refractive result that is stable.

Simon in U.S. Pat. No. 5,090,955 describes a surgical technique that allows for modification of the corneal curvature by inter-lamellar injection of a synthetic gel at the corneal periphery while sparing the optical zone. He does discuss an intra-operative removal of gel to decrease the volume displaced and thus adjust the final curvature of the central corneal region.

Siepser (U.S. Pat. No. 4,976,719) describes another ring-type device to either flatten or steepen the curvature of the cornea by using a retainer ring composed of a single surgical wire creating a ring of forces which are selectively adjustable to thereby permit selective change of the curvature of the cornea,—the adjustable means comprising a turnbuckle attached to the wire.

There are several mechanisms by which peripheral manipulation of the cornea affects anterior corneal curvature. The cornea, like most soft tissues, is nonlinear, viscoelastic, nonhomogeneous, and can exhibit large strains under physiologic conditions. The whole eye is geometrically extremely complex and the biomechanics technique capable of systematically modeling this reality is the finite element method which assumes small strains (a measure of deformity), homogeneity, and linear elastic behavior. Two simple mechanisms will be briefly described.

A simple example is helpful in understanding the first mechanism. Assume a loose rope R between two fixed points P1 and P2 as in FIG. 2(a), which forms a curve, the lowest point P being in the middle. Referring to FIG. 2(b), a weight w placed on the rope between the middle point P and one fixed point will cause the central portion of the rope to straighten 11. The cornea C demonstrated in FIG. 3(a) and FIG. 3(b) behaves similarly, the two fixed points, P1 and P2, analogous to the limbus of the eye and the weight W similar to the intrastromal implant 16 which, when inserted in the cornea in surrounding relation to the corneal central optical zone, causes the corneal collagen fibers to deviate around the implant. In essence, this deviation of the cornea around the peripheral implant caused by volume displacement in the peripheral cornea results in other areas of the cornea losing "slack", or relatively straightening 14.

Mechanical expansion of a corneal ring's diameter also flattens the central corneal curvature whereas constriction of the diameter steepens the central corneal curvature. A constricting or expanding implant is likely to cause a less stable refractive outcome because the inward or outward forces of the implant against the corneal stroma may gradually cause further lamellar dissection and dissipation of the forces. A more consistent outcome is likely to be achieved with varying the volume displaced in the peripheral cornea as described by Simon.

The second mechanism is aptly described by J. Barraquer in the following quote. Since 1964, "It has been demonstrated that to correct myopia, thickness must be subtracted from the center of the cornea or increased in its periphery, and that to correct hyperopia, thickness must be added to the center of the cornea or subtracted from its periphery." Procedures involving subtraction were called 'keratomileusis' and those involving addition received the name of 'keratophakia'. Intrastromal corneal ring add bulk to the periphery and increasing the thickness of the ring results in a more pronounced effect on flattening of the anterior corneal curvature by "increasing (thickness) in its periphery".

In the February, 1991 issue of Refractive and Corneal Surgery, T. E. Burris states that "the thickening effects of ICR implantation may prove most important for maintenance of corneal fattening" and that "new ICR designs must take into consideration thickness effects on corneal flattening.

Again, the ideal keratorefractive procedure allows all the advantages of eyeglasses or contact lenses, namely, being able to correct a wide range of refractive errors, accuracy or predictability, allowing reversibility in the event that the refractive state of the eye changes and it becomes necessary to adjust the correction again, yielding minimal complications, and associated with technical simplicity, low cost, and being aesthetically acceptable to the patient. The goal of refractive surgeons should be to achieve 20/20 uncorrected visual acuity with long-term stability in greater than 95% of patients. None of the currently available refractive surgery procedures generate this degree of accuracy or stability.

An easy procedure to post-operatively fine-tune the refractive correction and corneal curvature which is often influenced by changes in corneal hydration status, wound healing responses, and other unknown factors, is not available. Each of the techniques described suffers from a limited degree of precision. In this disclosure of the present invention, an easy method to adjust the refractive outcome after the corneal curvature has stabilized, a method that is minimally invasive, a method causing minimal stimulation of the wound healing processes, allowing repetitive adjustments as deemed necessary, and being almost completely reversible is described. It may make moot the pervasive issue of unpredictability and make obsolete the application of procedures which rely heavily upon nomograms to predict refractive outcome and are thus unable to adequately account for an individual's variable response to the procedure.

SUMMARY OF THE INVENTION

The present invention concerns the use of an adjustable intrastromal device adapted for implantation in the cornea and formed of at least three ring-shaped and flexible elongated strand-like filaments of a variable size. The strands have a radial cross-sectional shape that is circular or oval. These strands are implanted in the cornea in surrounding relation to the optical zone of the cornea. The strands maintain their proximity to one another by the presence of periodic bands, which encircle the strands. These bands are spaced apart from each other such that there are a total of at least three bands surrounding the strands. The corneal curvature is then adjusted by complete removal of one or more strands thus modifying the volume of peripheral corneal tissue displaced in a discrete fashion and resulting in steepening of the central corneal curvature and a myopic shift. This relatively simple adjustment for refractive correction can be performed with surgical instruments commonly available and requires minimal post-operative manipulation of the cornea and the implanted device. The apparatus of the invention is an adjustable implantable device and adapted to be inserted into the interlamellar space of the corneal stroma for the purpose of correcting refractive error. The peripheral corneal volume displaced by the device is easily discretely modified on multiple occasions following the initial surgery of implantation and thus allows for adjustment of the refractive outcome at a later date without necessitating the complete removal of the implanted device.

BRIEF DESCRIPTION OF THE DRAWINGS

FIG. 4(a) is a plan view of the split-ring form of the device of the invention;

FIG. 4(b) is a plan view of the arc-segment form of the device of the invention;

FIG. 5(a) is a plan view demonstrating bands on the split-ring form of the device of the invention;

FIG. 5(b) is a plan view demonstrating bands on the arc-segment form of the device of the invention;

FIG. 6(a) is a radial cross-sectional view of the device of the invention within the cornea of the eye;

FIG. 6(b) is a plan view of the device of the invention within the cornea of the eye;

DETAILED DESCRIPTION OF THE INVENTION

Figure 1A:
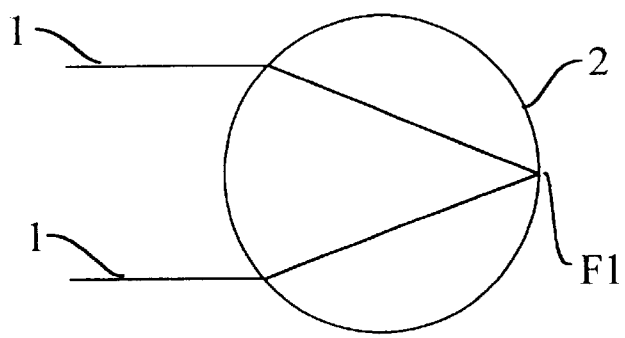
FIG. 1(a) is a schematic representation of an eye demonstrating light rays focusing on the retina.
Figure 1B:
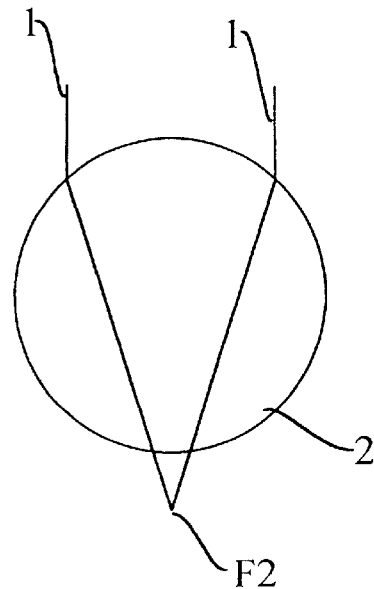
FIG. 1(b) is a schematic representation of a hyperopic eye.
Figure 1C:
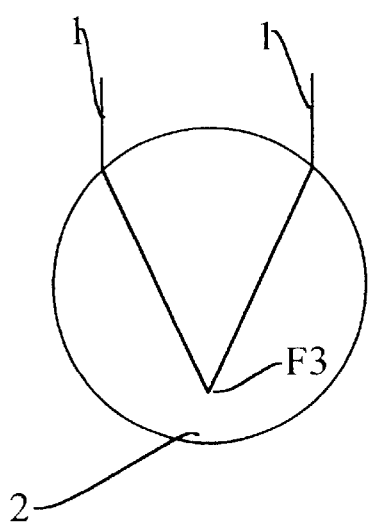
FIG. 1(c) is a schematic representation of a myopic eye.
Figure 2A:
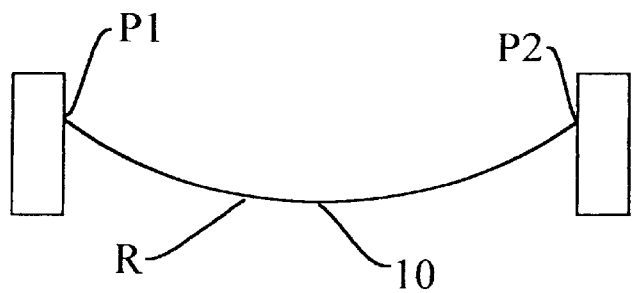
FIG. 2(a) is a schematic representation of a rope between two fixed points.
Figure 2B:
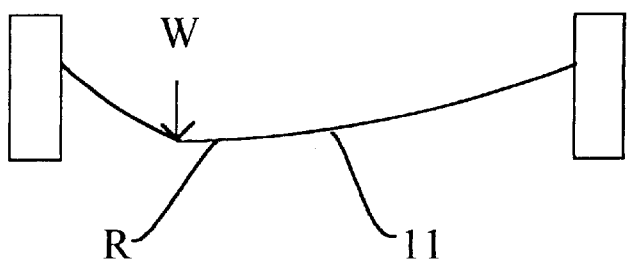
FIG. 2(b) is a schematic representation which shows the rope of FIG. 2(a) with the force3 of a weight applied to the rope between its midpoint and one of the fixed points.
Figure 3A:
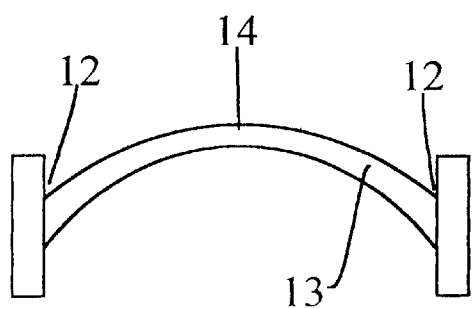
FIG. 3(a) is a schematic representation of the cornea of an eye wherein the cornea is fixedly attached at diametrically opposed points on the surrounding limbus.
Figure 3B:
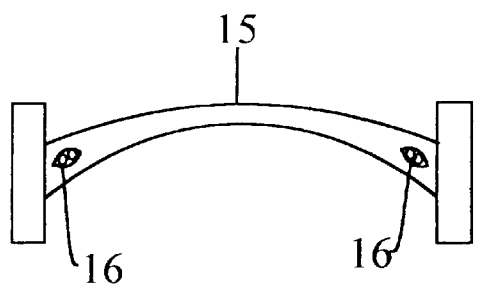
FIG. 3(b) is an illustration similar to FIG. 3(a) but showing the curvature effects produced on the cornea because of the presence of an intrastromal support implant in the cornea.
Figure 3C:
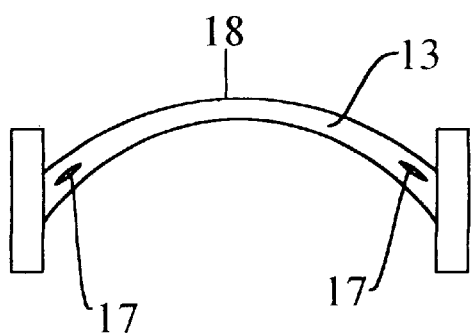
FIG. 3(c) is an illustration similar to FIG. 3(b) but showing the curvature effects on the cornea following removal of the intrastromal support implant from the cornea.

Referring more particularly to the drawings, there is shown in FIGS. 4–6 the apparatus of the present invention 20. The present invention concerns the use of an adjustable intrastromal device adapted for implantation in the cornea 13 and formed of at least three ring-shaped and flexible elongated strand-like filaments 16 of a variable size. The strands have a radial cross-sectional shape that is circular or oval. These strands are implanted in the cornea 13 in surrounding relation to the optical zone of the cornea as demonstrated in FIG. 6(b).

The device 20 is composed of at least three strands 16 of a bio-compatible plastic or polymer material such as polymethylmetbacrylate (PMMA), nylon, polypropylene, polyester, polyimide, or fluoropolymer resins. The strands can be any biocompatible material that is a flexible, filamentous structure and may be constructed from a resilient polymeric substance such as that described above but the preferred material is PMMA. Its composition material may be similar to those materials used in producing foldable or deformable intraocular lenses such as a silicone polymer, urethane polymer, acrylic polymer, or hydrogel. The strands consist of a flexible material, which is biocompatible, and more specifically, compatible with ocular tissues. The strands may also be composed of a porous polymer material such as a microporous polypropylene material. The strands may be composed of one or more natural or synthetic polymers. An example of a natural polymer that may be used is collagen.

The composition material of the strands may be any suitable plastic or polymer material such as that used in producing foldable or deformable lenses, silicone polymers, urethane polymers, acrylic polymers, polyesters, fluoropolymer resins, or materials used in soft contact lenses. It will be understood by those skilled in the art that, among polymers of acrylic esters, those made from acrylate ester monomers tend to have lower glass transition temperatures and to be more flexible than polymers of methacrylate esters. There are many other suitable polymeric materials, including but not limited to epoxy resins, polyamides, polyacetals, polycarbonates, polyethers/ether ketones, polyolefins, polyurethanes, polyvinylpyrrolidone, natural or synthetic rubbers, polysulfones, copolymers, and combinations of the above.

Examples of other medical devices composed of materials which be suitable for the shell of this invention include vascular graft tubing, dialysis tubing or membrane, blood oxygenator tubing or membrane, ultrafiltration membrane, intra aortic balloon, catheter, suture, soft or hard tissue prosthesis, artificial organ, and lenses for the eye such as contact and intraocular lenses. The surfaces of the strands are smooth and do not have raised or indented areas and do not intermesh with each other. This is important for ease of strand removal at a later date. The surface of the strands may also undergo surface modification by currently known techniques to decrease surface friction relative to each other and to the surrounding stroma in anticipation of possible later strand removal. A key element of this invention is attention to the details that facilitate strand removal from the cornea at a later date, such as surface modification.

In FIG. 4(a) is shown the device of the invention 20, consisting of at least three strands 16 in an annular configuration with two ends 21. FIG. 4(b) shows segments of strands 22 that are less than 360 degrees. The U.S. patent, "Adjustable Corneal Arcuate Segments", filed by this author in 1998, is included herein in its entirety by reference. It is anticipated by this author that the various segment shapes and arc lengths described in the "Adjustable Corneal Arcuate Segments" patent can also be applied to the device of the current invention in the treatment of astigmatism, hyperopic astigmatism, myopic astigmatism, and the adjustments thereof.

Referring to FIG. 5(a), in a sub-embodiment of the invention, the strands 16 have bands 23 that surround the strands. The purpose of the bands is to maintain the strands 16 in relative proximity to each other such that the radial cross-section of the device, as demonstrated in FIG. 6(a), has a generally oval configuration. It can be seen that strands of a circular radial cross-section do not easily stack on top of each other and will tend to spread apart from each other unless the strands are confined in relative proximity to each other by some means. The bands 23 serve the purpose of confining the strands such that the radial cross-section of the device is generally oval. The strands may be held together in relative proximity to each other by various other means such that following implantation the relative position of the strands to each other does not significantly change. The strands are maintained in their proximity to one another by the presence of periodic bands 23 that encircle the strands. These bands are spaced apart from each other such that there are a total of at least three bands surrounding the strands. Ideally, the bands will maintain the collection of strands in an oval cross-sectional shape. These bands are especially necessary in maintaining a given thickness of the strand collection when the individual strands have a circular cross-section. The encircling bands are positioned such that there are at least three bands for the 360 degrees and typically having 5 to 7 bands equidistant from each other. The bands may be composed of the same material previously described for the strands. The band may also be up to several millimeters in width. The bands are not physically attached to the strands, allowing the strands to be easily removed at a later date.

From FIG. 6(a), it can be seen that the strands 16 are confined in a generally oval shape by the walls 24,25 of the intrastromal annular channel. Thus, although bands may be useful, if the channel radial cross-sectional dimensions are similar to the radial cross-sectional dimensions of the device, the walls of the channel may suffice in maintaining the device in a generally oval cross section. If, however, the intrastromal channel is initially made larger than the radial cross-section of the device, the strands of the device will separate from each other and result in a device with a radial cross-section that is a flatter oval. The bands may be useful in this situation to maintain the radial cross-sectional shape of the device until the inner 27 and outer 26 diameters of the channel wall undergo healing and are not easily further delaminated.

Because the walls of the channel 24–27 undergo healing and will eventually form itself around the device confining the strands in a generally oval cross-section, it is not essential that the bands be composed of a permanent material. Although bands effectively accomplish their purpose of confining the strands within a certain shape, there are other methods of accomplishing the same goal. The strands may also be maintained in relative proximity to each other such that the radial cross-sectional shape of the device is generally oval, by the use of a biocompatible adhesive. The adhesive is preferably weak and necessarily temporary since it is anticipated that at least a single strand will later be removed, if necessary, to adjust the corneal curvature. The adhesion is required only until the intrastromal channel walls undergo healing around the implanted device. If a strand is to be later removed, it must not be attached to surrounding strands.

Strands 16 having a radial cross-sectional circular or oval cross-sectional shape have the greatest volume relative to its surface area. Thus, these strands also displace the greatest amount of peripheral corneal tissue relative to its area of contact with the corneal stroma-strand interface, thus allowing minimal disturbance of the strand-cornea interface while permitting maximum volume displacement alteration when the strand is later removed. If, as previously described, the strands are of a circular cross-sectional shape, the strands will not easily stack on top of each other but rather separate from each other within the peripheral lamellar corneal channel and result in less effect on the anterior corneal curvature. The collection of strands must be maintained in relative proximity to each other in order for the collection of strands to have a maximal stable refractive effect. For example, using strands with a circular cross-sectional shape, two strands that are stacked on two other strands will have more of a refractive effect than four strands each positioned one next to the other. If the corneal lamellar channel is completely filled with the circular cross-sectional strands, it is unlikely for the strands to shift significantly. However, if the channel cannot be completely filled with the circular cross-sectional strands, the strands will shift and spread apart. Also, because of the manner of strand implantation within the channel, it may be difficult to completely fill the channel with strands. A simple approach to this problem is the implantation of an expandable strand, such as that made of hydrogel, along with the other strands. Hydrogel expands by up to 70% with the absorption of water. Following implantation, the hydrogel strand expands such that all the strands combined completely fill the channel. Strands of the hydrated hydrogel are unlikely to be sufficiently strong to allow strand removal from the implanted cornea in the typical method. However, the strands composed of stronger materials may be removed from the peripheral cornea in the event of overcorrection.

Referring to FIGS. 6(a)–(b), the device 20 consists of at least three strands adapted to be implanted into the peripheral stromal cornea. The strands 16 are maintained in relative proximity to each other by the walls 24,25 of the annular corneal channel. The device is of a thickness and geometry such that when implanted it alters the central corneal curvature without intruding into the central optical zone of the cornea and without decreasing the diffusion of nutrients to the central cornea. It is of a size such that it can be readily inserted into the peripheral human cornea.

The radial cross section of a strand may be of various geometric shapes. However, the preferred embodiment has a radial cross-sectional shape that is circular or oval. The radial cross-sectional area of the strand can vary in dimension along its length. The device is composed of at least three strands, at least one of which is easily removable from the cornea at a later time. The device may be composed of strands of varying cross-sectional shape, cross-sectional area, and material composition. The advantage of a circular cross-section is that it allows the greatest peripheral corneal tissue volume displacement with the least strand surface area. Decreasing the amount of surface contact between the strand and the cornea allows each strand to be removed at a later time while minimizing the amount of disturbance to the strand-corneal stroma interface thus minimizing the possibility of a potentially unpredictable secondary wound healing response.

Figure 7A:
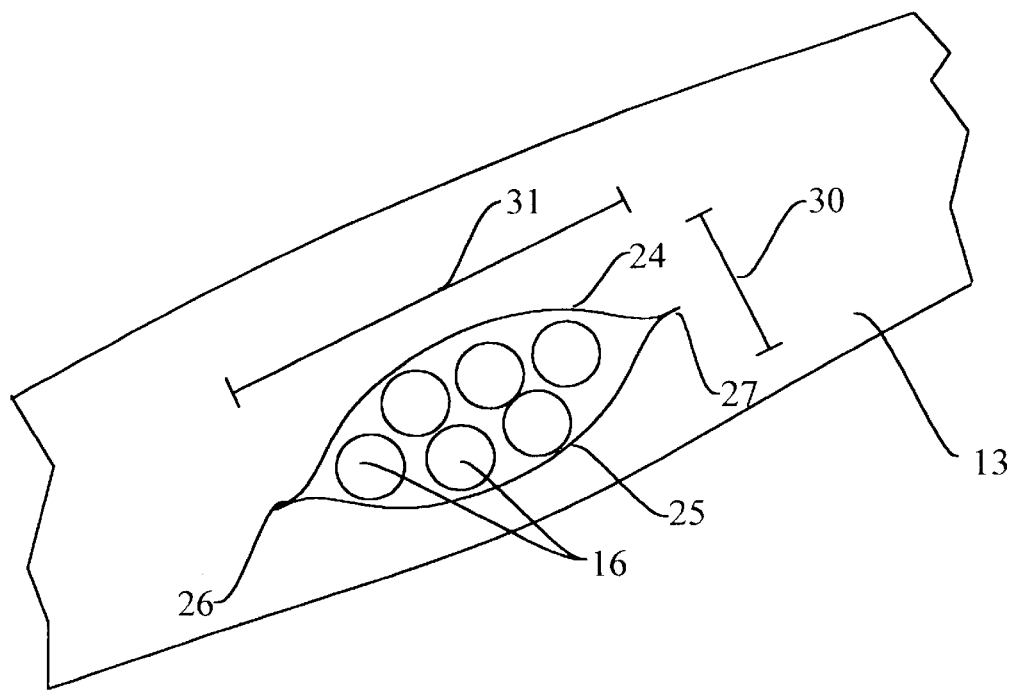
FIG. 7(a) is a radial cross-sectional view of the device of the invention within the cornea of the eye illustrating the dimensions of the device.

The range of dimensions of the peripheral corneal volume displacement provided by the strands as shown in FIG. 7(a) include a height of (30) of 0.1–1.0 mm, width (31) of 0.3 to 2.0 mm and an over-all diameter of 4.00 to 11.0 mm. A typical device, which is expected to correct myopia by approximately 3 diopters, has a width of 0.85 mm and height of 0.3 mm. The width is 0.85 mm and height is 0.3 mm. A device displacing corneal volume by this amount is expected to correct myopia by approximately 3 diopters. A device displacing greater corneal volume would be required for myopic correction of 4 diopters and a device displacing corneal volume by less than this amount required for myopic correction of 2 diopters. Of course, a particular individual may not have the exact same outcome as another individual for the same device size. Devices of lesser radial cross-sectional area are calculated to correct a smaller amount of myopia and devices of greater radial cross-sectional areas are calculated to correct a greater dioptric amount of myopia.

Figure 7B:
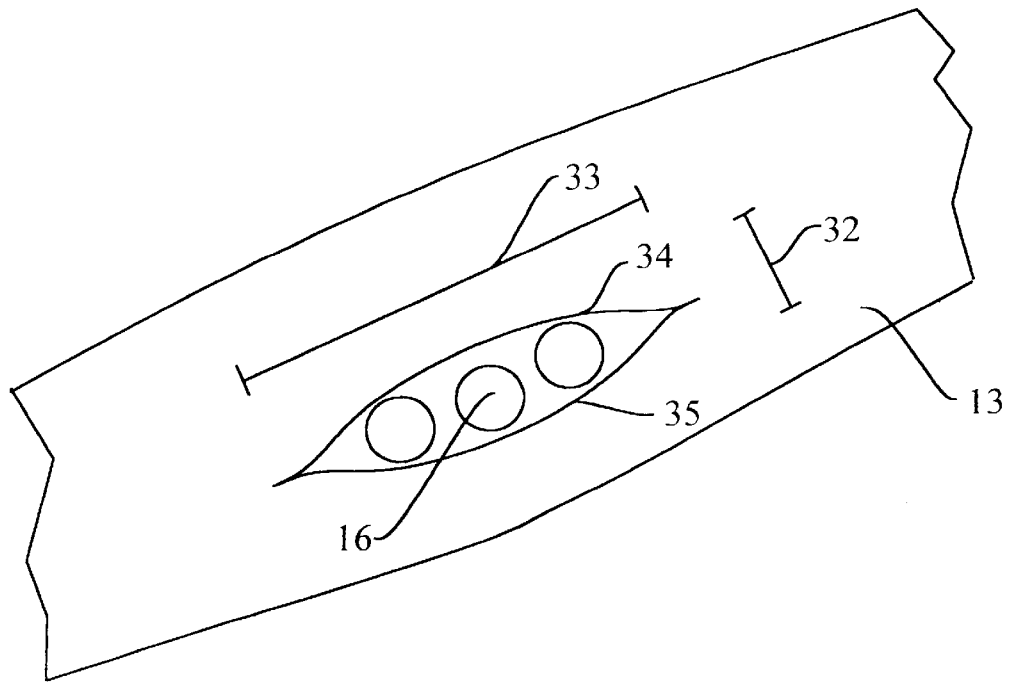
FIG. 7(b) is a radial cross-sectional view similar to FIG. 7(b) demonstrating smaller dimensions of the device following removal of several strands.

The process of strand removal from a device implanted in the cornea is later described. FIG. 7(b) demonstrates the change in peripheral corneal volume displacement following strand removal. It can be seen that the radial cross-sectional area circumscribed by the lamellar channel walls 24, 25 in FIG. 7(a) is greater than the radial cross-sectional area circumscribed by the lamellar channel walls 34, 35 in FIG. 7(b). Strand removal from the peripheral cornea thus allows a method of adjusting the anterior corneal curvature following device implantation.

The number of strands within the device and the radial cross-sectional size of the individual strands can be selected pre-operatively to minimize the number of strands that needs to be removed to effect a reasonable dioptric change. A strand may have a radial cross-sectional diameter of 0.02 to 1.0 mm in diameter. Formulas can be developed that predict the dioptric change expected following removal of a single strand of a given radial cross-sectional diameter while taking into consideration such factors as initial refractive error, refractive change effected by the particular implant, number of strands in the initial implant, and corneal implant diameter. The radial cross-sectional size of strands is chosen such that removal of a single strand will effect a steepening in corneal curvature by approximately 0.1 to 1.00 diopter.

Given an initial myopic patient, the outcome can be overshot by over 100% of the initial refraction and the resultant hyperopia still reasonably managed by strand removal alone. Over-treatment resulting in hyperopia is a significant disadvantage in most kerato-refractive procedures. In radial keratotomy the wound healing processes occur over a period of years and there is often a progressive hyperopia. Patients who become symptomatically hyperopic after surgery are extremely unhappy. Therefore most surgeons use nomograms that attempt to achieve a slight under-correction. Concerning photorefractive keratectomy, in one study, it was found the main reason patients did not have their second eye corrected with PRK (given that their first eye was corrected with PRK) was because of dissatisfaction with the hyperopia in their operated eye. The technique described herein easily corrects over-correction of myopia, which results in hyperopia.

The device consists of three to ten strands 16 of varying diameter and composition. Each strand can vary from 0.02 mm in diameter to 1.0 mm in diameter. The strands may be clear or colored. The strands may have a prefabricated loop at one end which would facilitate removal of the strand by using an instrument having a small hook at the operative end with which the loop can be snared, as previously described in this inventor's U.S. patent application Ser. No. 08/829,846, filed Apr. 1, 1997. Instead of a loop, the strand end may have some other configuration such as a rounded or thickened end that would also facilitate grasping the strand. The loop also aids in preventing surrounding rings from being pulled out simultaneously by providing resistance at the open end. The strands may also have a small identifying mark such as a horizontal scratch or notch versus a vertical scratch or notch at a predetermined location so the various marks can be correlated to the actual diameter of the strand. In the event that strand removal is later required, this marking system would identify larger or smaller strands and thus guide the surgeon in the amount of refractive reversal he can expect.

The device consisting of an annular collection of strands with several encircling bands is implanted into a circular lamellar channel formed at ½ to ⅔ corneal depth. A knife is used to make a small midperipheral corneal incision. The surface of the cornea is cut only at this incision. A Suarez spreader or other lamellar dissecting instrument is introduced into the bottom of the incision and a small lamellar channel created. Application of a suction ring may be used to fix the globe while an 8–9 mm outer diameter lamellar channeling tool introduced through the incision into the lamellar channel is rotated to produce an annular channel around the corneal midperiphery at ½ to ⅔ corneal depth.

Figure 8A:
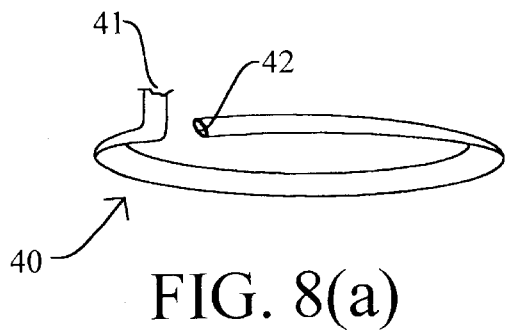
FIG. 8(a) is a perspective view of a hollow instrument for insertion of the device of the invention.
Figure 8B:
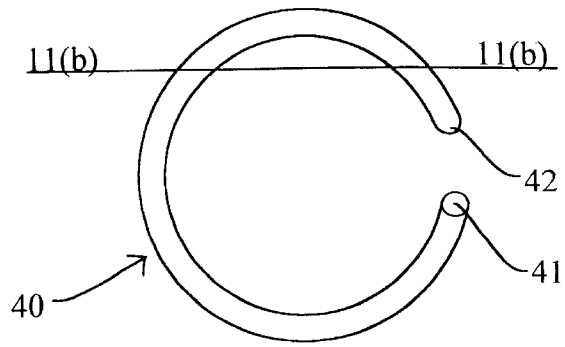
FIG. 8(b) is a plan view of the instrument of FIG. 8(a)
Figure 8C:
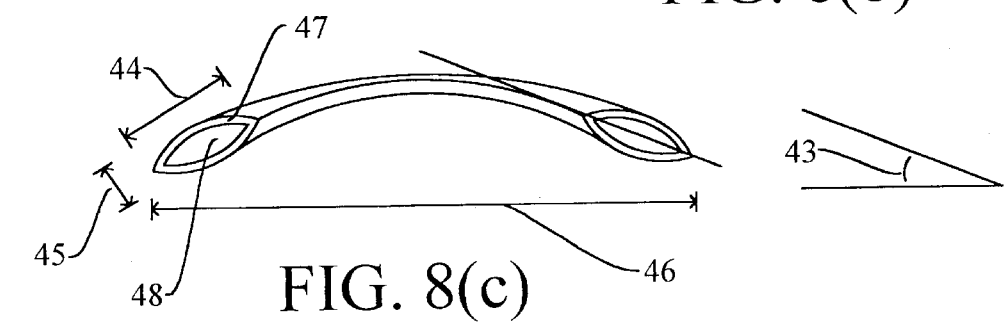
FIG. 8(c) is a perspective view of a cut through the tube portion of the instrument of FIG. 8(a)
Figure 8D:
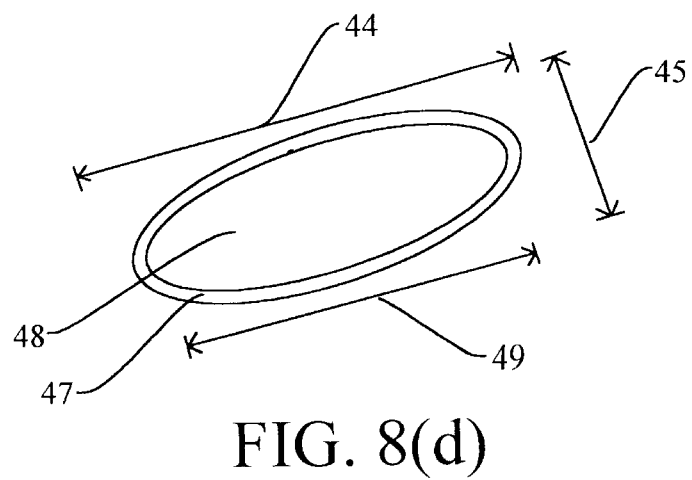
FIG. 8(d) is an expanded view of the cut portion from FIG. 8(c), demonstrating the hollow nature of the instrument.
Figure 9A:
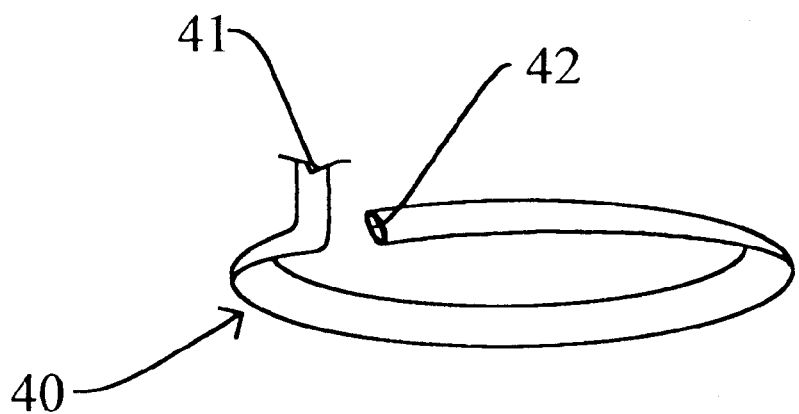
FIG. 9(a) is a similar view to FIG. 8(a)
Figure 9B:
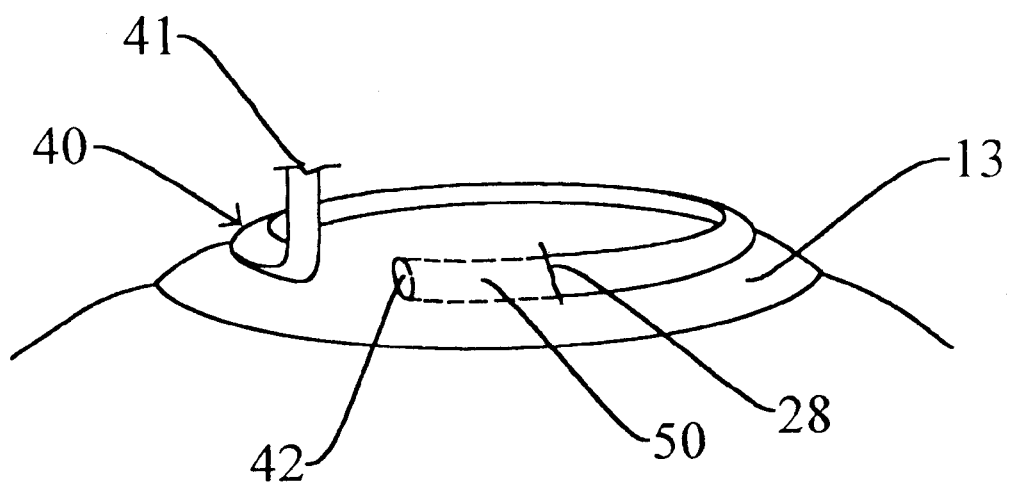
FIG. 9(b) is a view of the instrument in FIG. 9(a) containing the device of the invention in the process of insertion within the cornea of an eye.

There are several approaches to device insertion. Referring to FIG. 8, the device may be delivered into position by an instrument 40. The instrument is circular in shape and can be inserted into a previously formed annular intrastromal lamellar channel. The circular portion of the instrument to be inserted into the channel is hollow 48. The leading end 42 of the instrument demonstrates its hollow nature. The hollow compartment of the instrument is filled with the strands of the device and the instrument is inserted into the pre-formed annular lamellar channel. FIG. 8(c) shows that the instrument has a conic angle 43 similar to that of the peripheral cornea. FIG. 8(d) illustrates the typical dimensions of the radial cross-section of the instrument which are similar to the dimensions for the device. Referring to FIG. 9(b), insertion of the instrument, containing within it the strands of the device, is illustrated. The leading end of the instrument 42 is inserted into a pre-formed lamellar channel through the anterior corneal incision 28. After complete insertion of the instrument, the strands of the device within the instrument's hollow tube are grasped and the instrument reversibly rotated and removed from the cornea of the eye leaving the strands of the device in place.

Figure 10A:
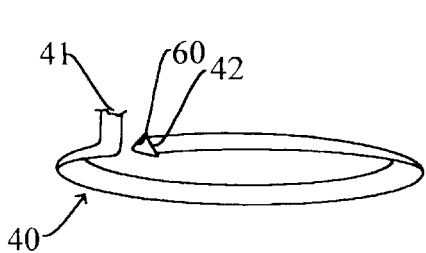
FIG. 10(a) is a perspective view of the surgical instrument of FIG. 8(a) with a leading segment attached to the leading end of the instrument.
Figure 10B:
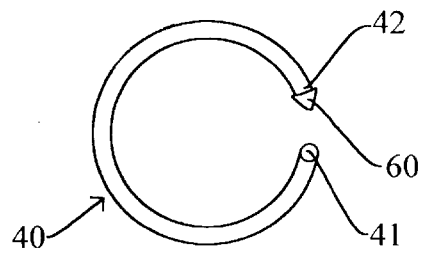
FIG. 10(b) is a plan view of the surgical instrument of FIG. 10(a) with a leading segment positioned at the leading end of the instrument.
Figure 11A:
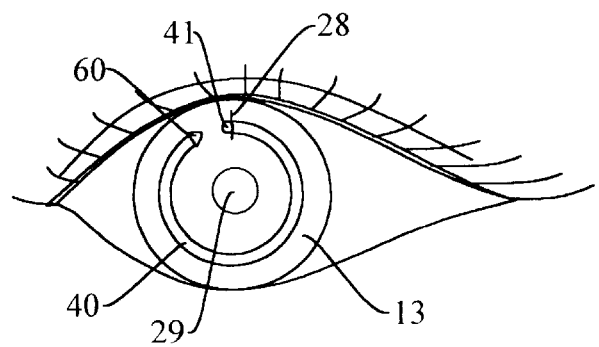
FIG. 11(a) is a plan view of the surgical instrument of FIG. 10(a) almost completely inserted into the intrastromal annular lamellar channel of the cornea.
Figure 11B:
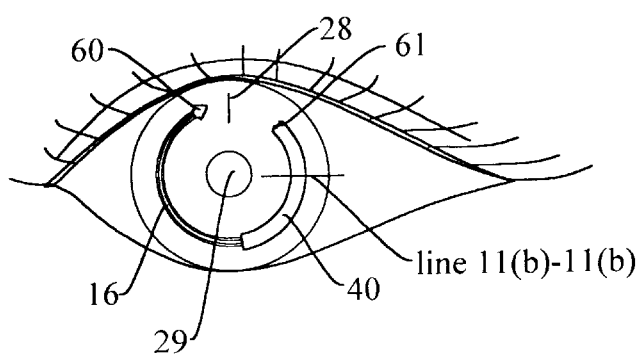
FIG. 11(b) is a plan view of the instrument of FIG. 11(a) partially removed from the cornea of the eye and the ring device of the invention partially positioned within the lamellar channel of the cornea.
Figure 11C:
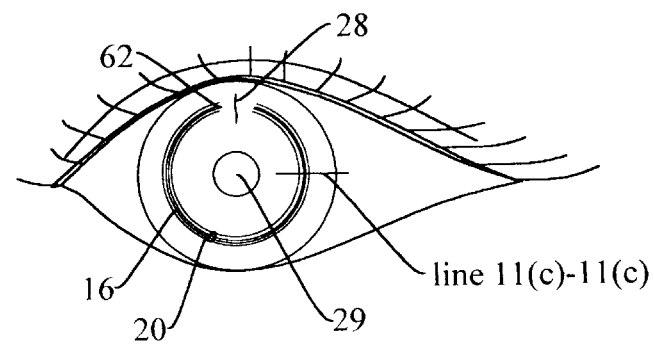
FIG. 11(c) is a plan view of FIG. 11(b) after the instrument has been completely removed, the device of the invention in position within the intrastromal annular channel of the cornea, and the leading segment removed from the device of the invention.

FIGS. 10, 11 demonstrate another aspect of the insertion instrument. FIG. 10(a) shows the instrument, similar to that previously described in FIG. 8. However, the instrument has a leading wedge segment 60. The wedge segment is attached to the device contained within the body of the instrument. FIG. 11(a) illustrates the instrument 40 with the leading wedge segment 60, completely inserted within the previously formed lamellar intrastromal channel. FIG. 11(b) demonstrates partial removal of the instrument 40. The complete instrument is not illustrated to ease visualization 61. The wedge segment 60 easily permits forward progress but resists backward movement. Thus, as the instrument is slowly withdrawn, the wedge segment which is attached to the strands maintains its position. Since the wedge segment is attached to the strands, the strands are removed from the instrument as the instrument is removed from the cornea. Alternatively, the wedge segment may be grasped by a forceps or some other means through the incision 28 while the instrument 40 is being removed. Referring to FIG. 11(c), following implantation of the strands, the wedge segment is detached from the leading end of the strands 62.

Figure 12:
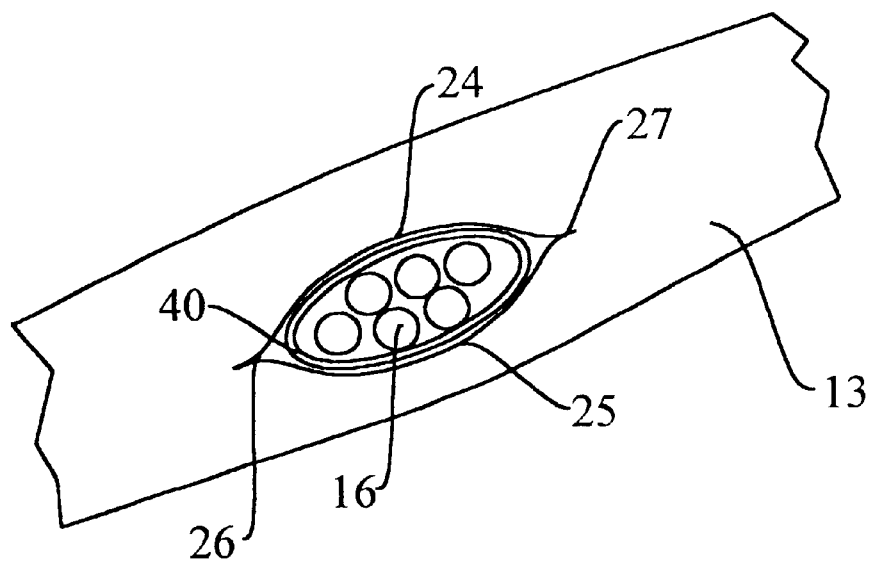
FIG. 12(a) is a radial cross sectional view of the line 11b—11b from FIG. 11(b) which shows the instrument within the lamellar channel and the ring device of the invention within the instrument.
FIG. 12(b) is a radial cross sectional view of the line 11c—11c from FIG. 11(c) which shows the ring device of the invention within the lamellar channel of the cornea.
Figure 12B:
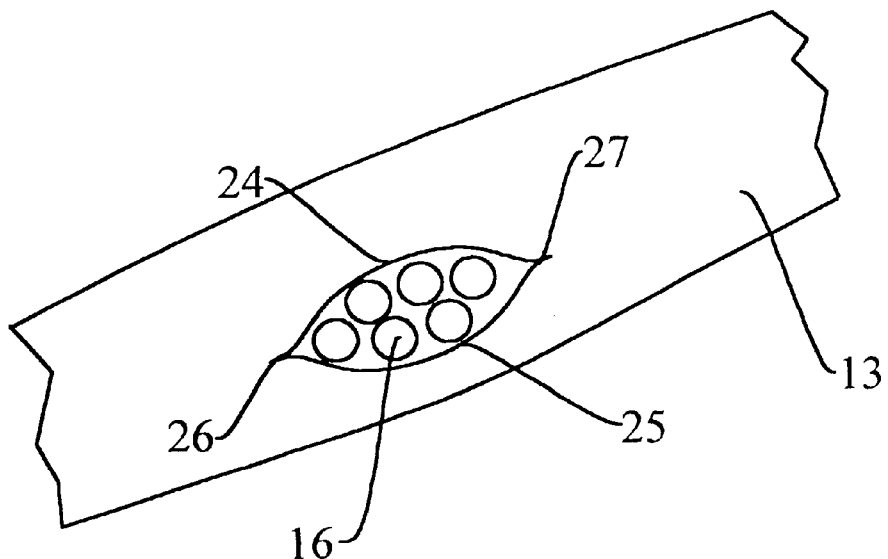

FIG. 12(a) demonstrates a radial cross-section through line 11(b)—11(b). The instrument 40 can be seen within the lamellar walls 24, 25 of the cornea. The strands 16 can be seen inside the hollow chamber of the instrument. FIG. 12(b) demonstrates a radial cross-section of line 11(c)—11(c) after the instrument has been completely remove, leaving the strands of the device in position within the lamellar channel.

Figure 13:
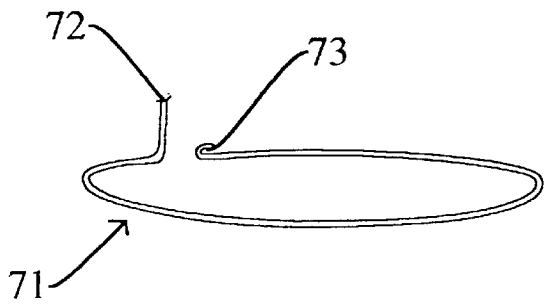
FIG. 13 is a perspective view of a circular hook instrument for insertion of the device of the invention.
Figure 14A:
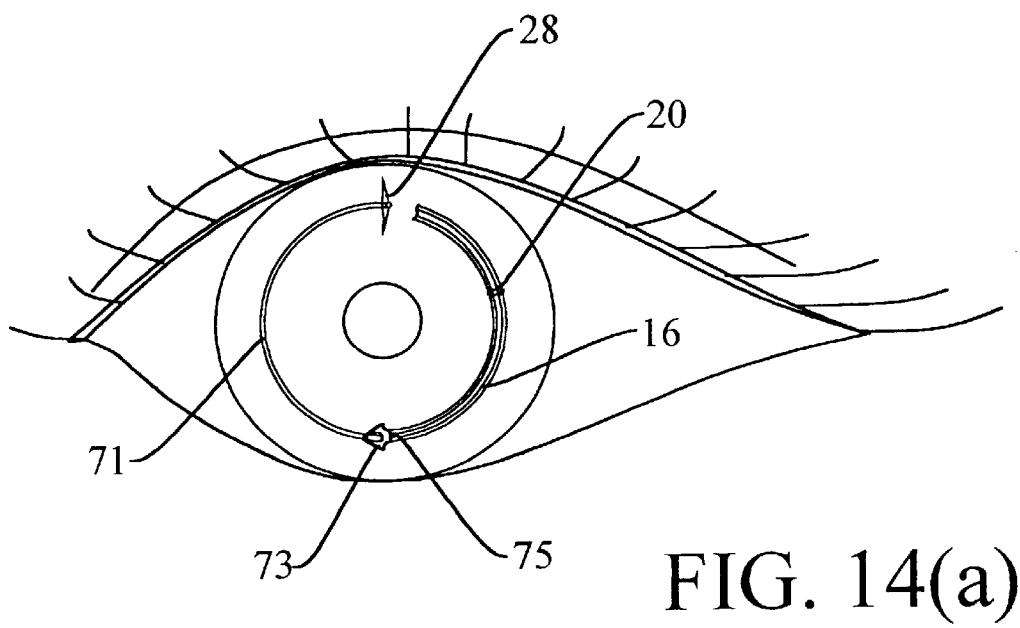
FIG. 14(a) is a plan view of the instrument of FIG. 13 partially inserted into the cornea of the eye and the ring device of the invention partially positioned within the lamellar channel of the cornea.
Figure 14B:
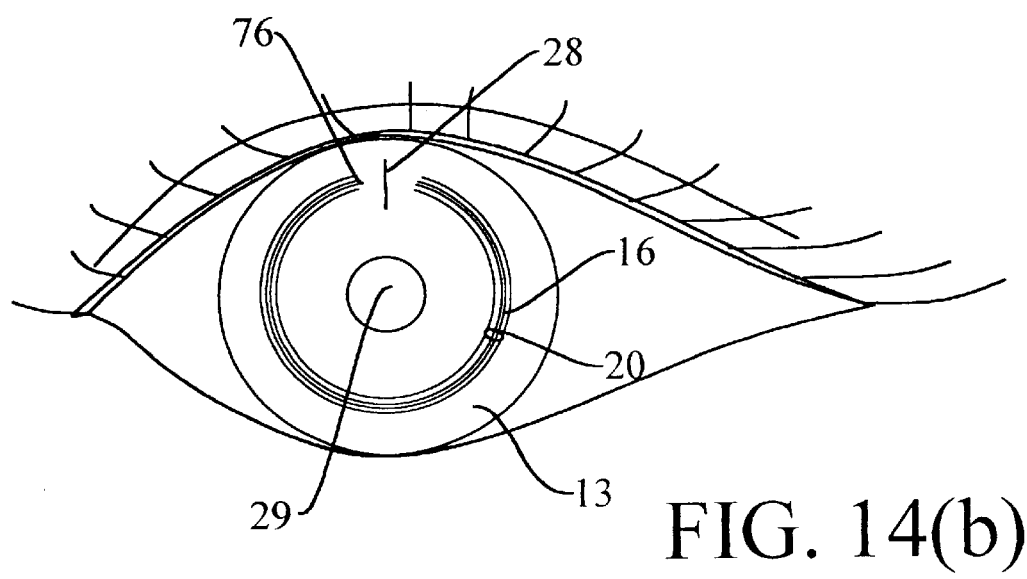
FIG. 14(b) is a plan view of FIG. 14(a) after the instrument has been completely withdrawn from the lamellar channel, the ring device of the invention completely positioned within the intrastromal annular channel of the cornea, and the leading segment removed from the device of the invention.

Referring to FIGS. 13–14, the device may be pulled into position within the previously formed lamellar channel. The instrument 71 has an annular portion that can be inserted into the previously formed annular channel, a handle portion 72, and a leading end hooked portion 73 to which the device can be attached. The leading end of the instrument may have a hook 73, forcep jaws, or other attachment means whereby the device can be attached and pulled into position. In this method, the instrument 71 is inserted into the annular lamellar channel counter-clockwise and the device inserted in a clockwise fashion. The leading end of the instrument 73 is rotated into the annular channel until the leading end of the device 75 can be fixed onto the leading end of the instrument 73. Typically, this attachment occurs with the instrument almost completely inserted and the device only partially inserted. The instrument is then rotated in a direction to remove the instrument thus progressively advancing the device into position within the annular channel.

Figure 15A:
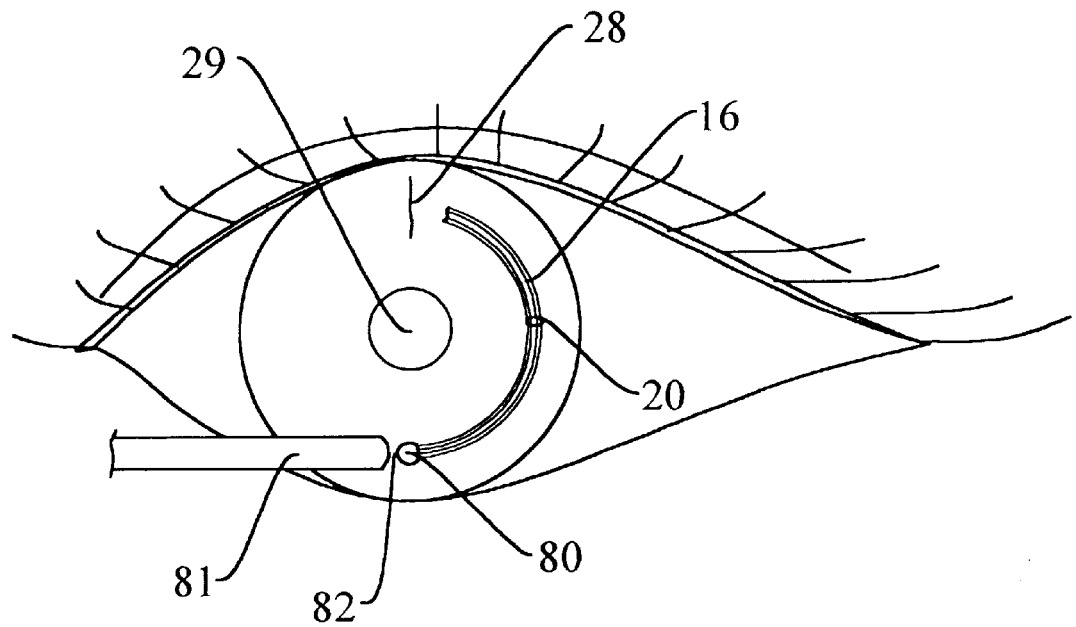
FIG. 15(a) is a plan view of the ring device of the invention halfway inserted into the cornea using a magnetic instrument to pull the ring device into position within the lamellar channel of the cornea.
Figure 15B:
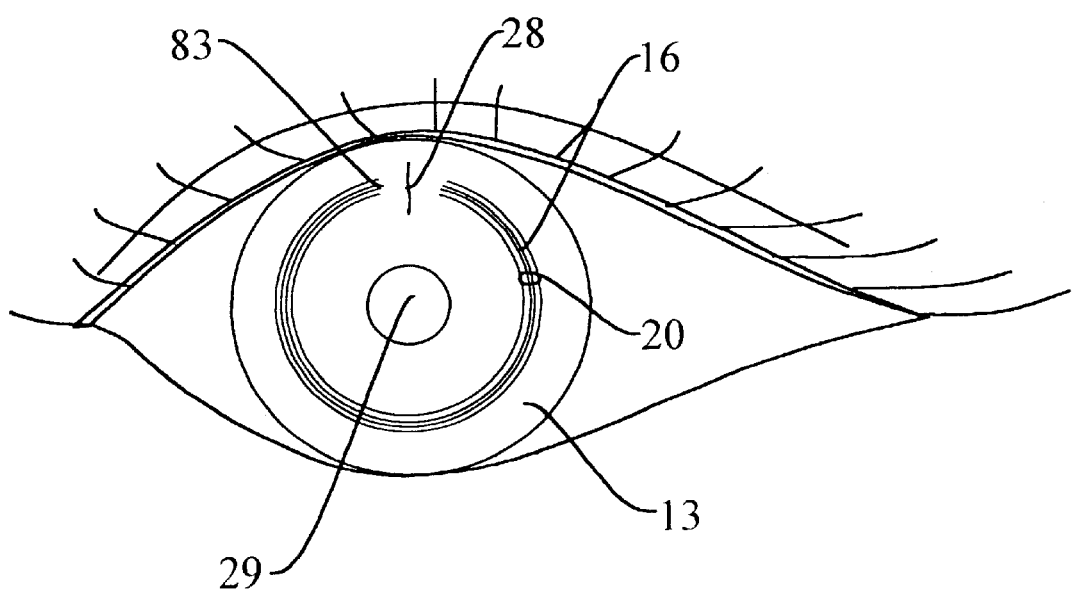
FIG. 15(b) is a plan view similar to FIG. 15(a) after the ring device of the invention has been completely inserted and the leading segment removed from the device of the invention.

Referring to FIG. 15, the device may also be pulled into position within the annular lamellar channel using magnetic forces. The head of the device has attached a metal segment 80 with smooth surfaces. The metal segment is made of a material, such as iron, that is attracted to a magnet. The device is partially inserted into the pre-formed lamellar channel. A magnet 81 is then used at a point above the cornea anterior to the clip. The magnet 81 is rotated in a circular fashion such that the clip follows the annular lamellar channel and the device 20 is progressively pulled into position. After complete insertion, the head of the device containing the clip is removed from device 83.

Figure 16:
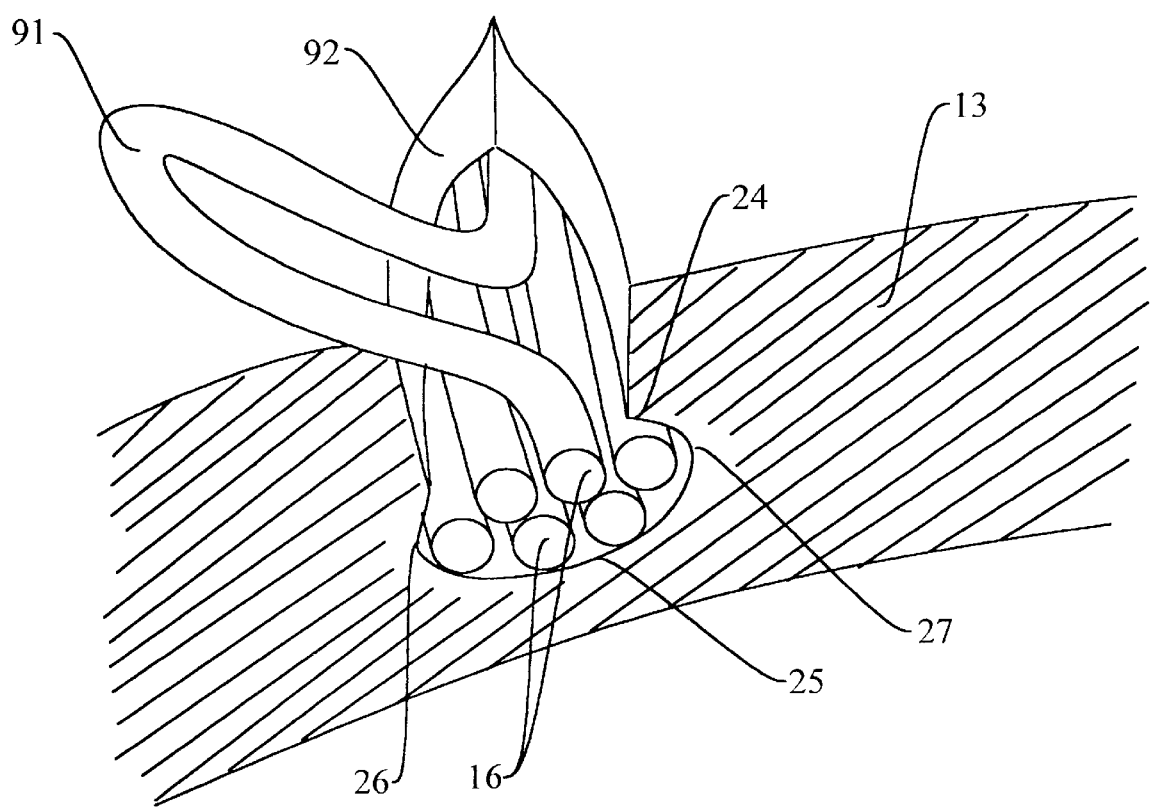
FIG. 16 is a perspective view of a radial cross section of a cornea containing the ring device of the invention, at a point where an anterior incision into the cornea has been made to facilitate removal of a strand from the ring device of the invention.

Referring to FIG. 16, strand removal 91 from the cornea 13 can be accomplished at the time of surgery with an intraoperative keratoscope to guide the refractive change. However, most of the benefit from adjusting the peripheral corneal volume displaced by the strands will occur at a time after corneal edema from the surgical procedure has resolved and the refractive effect has stabilized. Strand removal is accomplished by making an incision 92, either radial or horizontal, into the anterior cornea at a site near the strands. This incision may be made at the initial incision site or at any other site on the cornea anterior to the strands. Preferably, the incision site is made 180 degrees away from the initial incision site at a location 180 degrees away from the two ends of a strand so that the original incision is left undisturbed. The incision is made through the upper lamellar channel wall 24 such that the strands can be accessed. A strand 91 can be removed from the incision site by a forceps type instrument or an instrument with a small hook at the end such as an iris hook. Post-operative adjustments are rendered simple and easy requiring only strand removal and avoid the complications of re-operation concomitant with most kerato-refractive procedures. The decrease in amount of peripheral corneal tissue displaced following removal of strands is important in effecting the refractive adjustment.

This postoperative adjustment can compensate for an inadequate preoperative implant choice, for corneal hydration intra-operatively which results in a different corneal curvature after corneal hydration status changes post-operatively, for an unexpected wound healing response in the periphery to the implant, and for later refractive changes caused by unknown factors. This postoperative adjustment is made possible by the implantation into the peripheral corneal stroma several strands which can easily be removed thus modifying the volume of peripheral corneal tissue displaced by the strands and resulting in increased corneal curvature.

Strand removal from the peripheral cornea is more easily accomplished than complete removal of a ring that displaces a comparable amount of corneal tissue as the multiple strands. Strand removal also allows a more simple adjustment than complete removal of the ring followed by re-implantation of a smaller or larger ring. Strand removal is also expected to disturb the stromal-implant interface less than complete removal of the whole ring, thus minimizing the effects wound healing and edema will have on the adjustment. Circular cross-sectional strands displace the most corneal tissue relative to its corneal contact and thus for a given peripheral corneal volume displacement change disturbs the surrounding cornea the least.

Flat cross-sectional strands have a large area of corneal contact and thus its removal causes maximal disturbance of the surrounding cornea for a slight peripheral corneal volume displacement decrease. A flat strand has a relatively large area of contact between the strand and the corneal tissue relative to the amount of peripheral corneal volume displacement it effects. This large area of contact between the strand and the corneal stroma becomes problematic when an attempt is made to remove the flat strand at a later date after wound healing in the area around the ring has stabilized. With the removal of the flat strand, a relatively large area of the interface between the corneal stroma and the ring is disturbed. The shearing of a large portion of this interface with removal of a flat strand will disrupt the surrounding corneal tissue causing more edema and resulting in a less predictable refractive result. Minimal disturbance of the ring-cornea milieu is crucial to the success of "fine-tuning" a refractive outcome. A postoperative adjustment causing minimal wound healing appears to be a necessary adjunct to any method that seeks to meet the criteria for an ideal kerato-refractive procedure.

Depending on the amount of refractive error, an appropriate device varied in strand radial cross-sectional shape, size, composition, number, and length, is chosen. The size of the device is chosen such that the range of over-correction or under-correction secondary to individual variability of response to surgery may be comfortably corrected (not requiring removal of all of the strands) by the methods described. The factors described above are chosen prior to insertion of the implant. The more peripherally in the cornea the device is placed, the less the refractive effect. Adjustable devices placed closer to the central cornea can potentially correct up to 20 diopters of myopia. Devices placed at a lesser depth within the corneal stroma are also expected to have a greater refractive effect. The ideal embodiment, given the preoperative refractive state and other pertinent data, is chosen prior to operating and then that embodiment further manipulated at a later time as necessary to determine the ideal curvature.

In a simple adaptation of this technique, this device may be used to correct astigmatism. Curvature variation of the anterior surface of the cornea is responsible for the majority of cases of astigmatism. The light rays converge upon more than one plane and no one principal focus is formed. Astigmatism ordinarily depends on the presence of toroidal instead of spherical curvatures of the refractory surfaces of the eye. It thus becomes obvious that to correct astigmatism certain areas of the cornea must necessarily be corrected to a greater degree than other areas. The strands can be varied in thickness along its circumference with the thicker strand areas displacing a greater amount of peripheral corneal tissue and corresponding to the areas of the cornea having a steeper slope and requiring greater correction. Also, the strands are not necessarily 360 degrees in length. The U.S. patent, "Adjustable Corneal Arcuate Segments", filed by this author in 1998, is included herein in its entirety by reference.

It is anticipated by this author that the various segment shapes and arc lengths described in the "Adjustable Corneal Arcuate Segments" patent can also be applied to the device of the current invention in the treatment of astigmatism, hyperopic astigmatism, myopic astigmatism, and the adjustments thereof.

It is therefore to be appreciated that by use of the present invention, the disadvantages of traditional refractive surgery procedures are avoided, such as 1) progressive hyperopia with radial keratotomy. Hyperopia in any refractive procedure is a generally worse outcome because the patient does not have clear vision at any range and because hyperopia is much more difficult to correct. The described procedure is particularly well suited to adjust a hyperopic refractive outcome. 2) The irreversibility of radial keratotomy and laser ablation surgeries. 3) Surgical manipulation of the central visual axis with the potential for scar and stromal haze formation following laser ablation procedures. 4) The need for chronic use of steroid drops with its accompanying complications such as cataract and glaucoma. 5) Regression with laser ablation procedures, especially following re-operation. 6) Reduction of positive sphericity with RK and laser ablation which may result in increased image aberration. 7) The invasiveness of laser in-situ keratomileusis. 8) Lack of precision and predictability with all current procedures. 9) The possible need for repetitive explanting and implanting of ICR'S, which may cause shearing of corneal peripheral channel lamellae with associated decrease in effect and also scar formation.

The last point requires further elaboration. Methods to adjust ring thickness have been described in the prior art. These methods are only discussed in relation to adjusting the ring thickness during implantation, not post-operatively. Attempts to adjust the thickness of the ring are most useful after corneal curvature has essentially stabilized. Adjustments of devices that have been described in the prior art would necessarily require rotation of the ring with resultant shearing of the complete corneal-ring interface. Rotation of the whole ring would be required to allow more or less overlap of the individual ring parts thus increasing or decreasing ring thickness. This shearing of the corneal tissue in the immediate vicinity of the ring may alter the corneal curvature in an unpredictable fashion and probably also cause more scarring with possible unpredictable long-term effects. In the embodiment that is described in this article, the device volume is adjusted with less disturbance of the surrounding tissue. There is some disturbance of the corneal-strand interface but only in the vicinity of the strand that is removed while the other strands and surrounding cornea is relatively undisturbed. Also, the additional shearing of the cornea caused by re-implanting another complete ring is avoided. In conclusion, a slight decrease in volume of peripheral corneal tissue displaced by the adjustment described is not only easier to perform, but also expected to have a much more predictable effect.

Most refractive surgery procedures use nomograms to calculate the correction required and cannot completely account for an individual's variable response to refractive surgery. Oftentimes, an enhancement procedure with all its unpredictability is relied upon to correct the residual refractive error, with its concomitant increase in complication rate and scar formation. This new espoused device allows for the fact that individual tissue response to the calculated correction may not be completely predictable, and permits easy adjustments at the time of surgery and more importantly, at a later date after corneal hydration and would healing responses have stabilized, by simple strand removal from the implanted device. The nature of these adjustments minimally disturb the implant-corneal interface (unlike the explantation of the ICR) and will thus allow a much more predictable adjustment. In addition, when correcting myopia, a hyperopic outcome is very difficult to correct with any of the current kerato-refractive procedures and overcorrection of myopia does occur. In this invention, a hyperopic outcome is relatively easily reversed by ring removal from the implanted device. Typically, in most kerato-refractive procedures for myopia, the surgeon aims for a slight under-correction because of the wish to avoid a hyperopic outcome. The ease with which a hyperopic outcome is adjusted with the device of the present invention enables the surgeon to aim for full correction, thereby obtaining the full benefit of the nomogram, and resulting in a higher percentage of patients with the desired refractive outcome even without a modification of the device. The surgeon may even choose to slightly overcorrect followed by a modification.

Figure 17A:
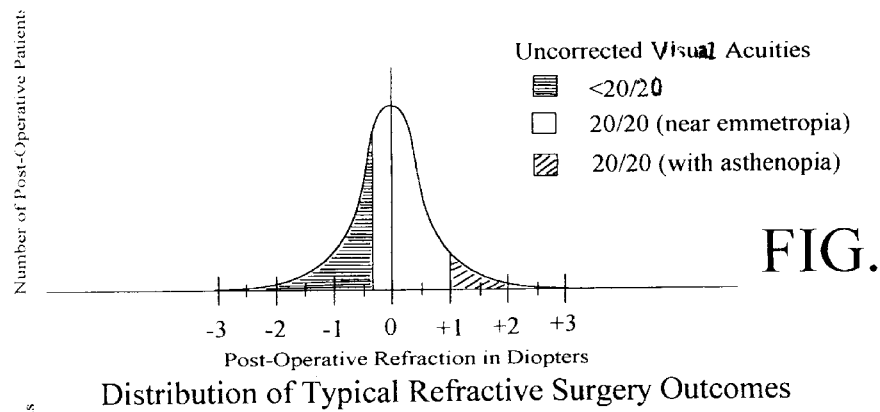
FIG. 17(a) is a graph showing the distribution of typical refractive surgery outcomes.
Figure 17B:
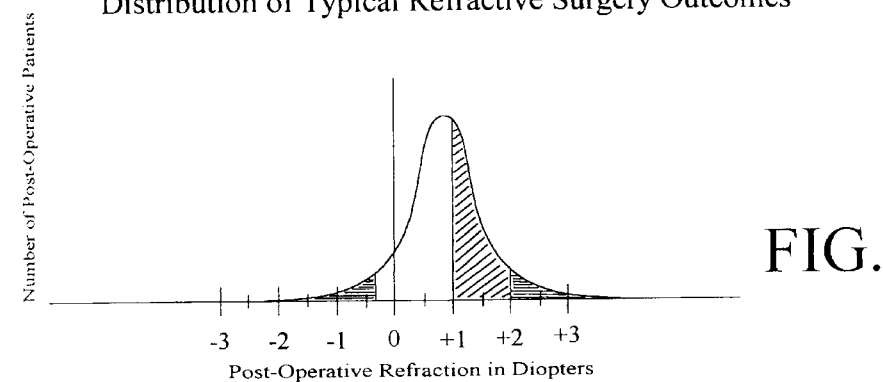
FIG. 17(b) is a graph showing the expected distribution of refractive surgery outcomes with hyperopic over-correction.

Referring to FIG. 17(a), it can be seen that there are many more patients with an uncorrected visual acuity of 20/20 on the right side (hyperopic, over-corrected) of the graph. The problem is that only 50% of patients achieve an uncorrected visual acuity of 20/20. Referring to FIG. 17(b), it becomes obvious that the easiest way to increase the percentage of patients achieving 20/20 is to shift the curve to the right. This means a higher percentage of over-corrected patients but also a much higher percentage achieving uncorrected vision of 20/20. Patients on the left side of the graph can be re-treated for their residual myopia. Because there are fewer options after being over-corrected, it is unethical to shift the curve to the right, even though a much higher percentage achieves 20/20. Also, even the patients who are on the right side of the graph and do see 20/20 now, will become presbyopic and will not have clear vision at any distance without glasses in the future.

Figure 17C:
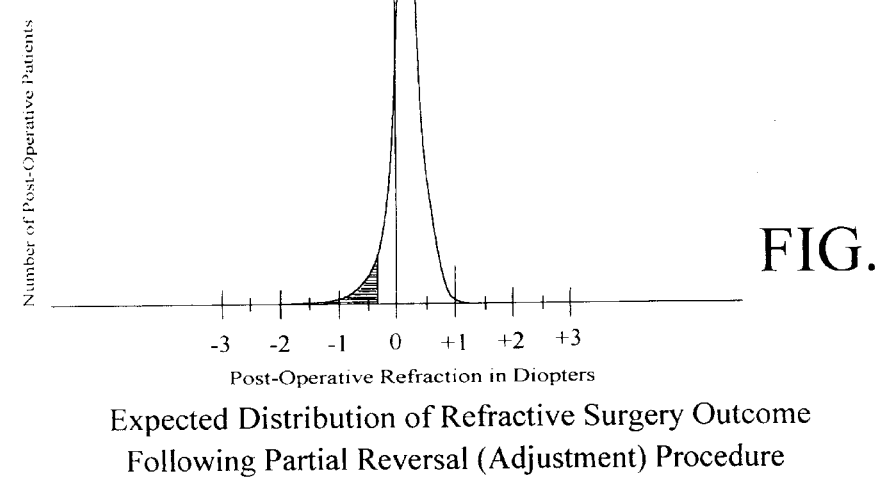
FIG. 17(c) is a graph showing the expected distribution of the ring device of the invention outcomes following an adjustment procedure.
Figure 18A:
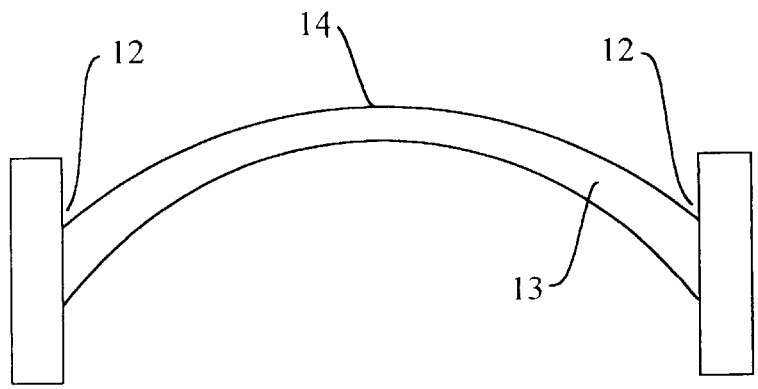
FIG. 18(a) is a schematic representation of the cornea of an eye wherein the cornea is fixedly attached at diametrically opposed points on the surrounding limbus.
Figure 18B:
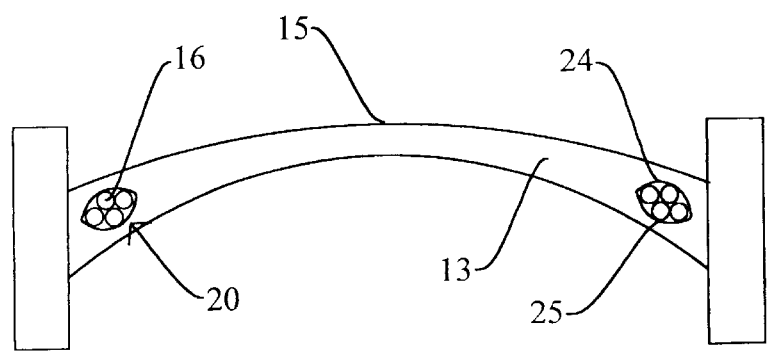
FIG. 18(b) is an illustration similar to FIG. 18(a) but showing the curvature flattening effects produced on the central cornea because of the presence of the ring device of the invention in the peripheral cornea.
Figure 18C:
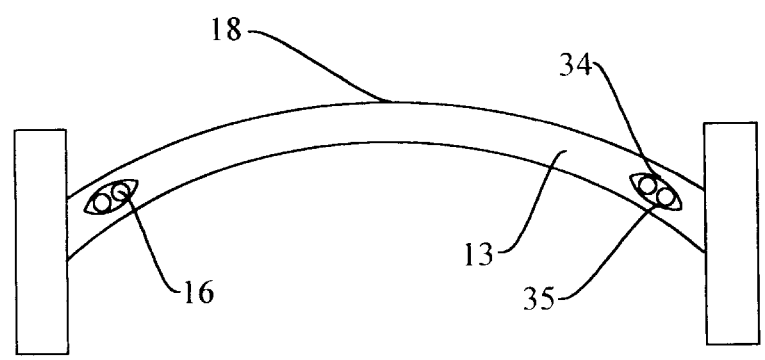
FIG. 18(c) is an illustration similar to FIG. 18(b) but showing the partially re-steepening effects on the central corneal curvature following removal of two strands from the implanted ring device of the invention.

FIG. 17(c) demonstrates the usefulness of a refractive procedure that can be partially reversed after the initial procedure. Assuming that a refractive procedure can easily be partially reversed after the initial procedure, the curve can safely be shifted to the right. All the patients in FIG. 17(b) who are >1.0 diopter overcorrected can undergo a partial reversal by simple strand removal. Even if only slightly hyperopic, if the patients become symptomatic, they may choose to undergo a partial reversal. This results in a much narrower distribution of patients and a distribution of patients that surrounds emmetropia. Another fortunate but coincidental outcome of this particular refractive strategy is that greater than 90% of patients may have an uncorrected visual acuity of 20/20 even prior to the adjustment procedure. This surgical strategy of shifting the nomogram and over-correcting patients' refractive error so that almost all patients are initially 20/20 without correction has not been used in the past with other keratorefractive procedures because of the fewer surgical options to correct the resultant hyperopia.

Dr. R. Eiferman in the Journal of Refractive and Corneal Surgery states that "if we can regulate the amount of tissue that is either added to or subtracted from the cornea and control the biological response, we may then be able to optimize refractive surgery". The ideal method to control the biological response is to minimally disturb corneal tissue, thus minimally inciting a wound healing response.

Dr. K. Thompson, in the same Journal asks, "will it be possible for a refractive surgery technique to bypass the variable effects of corneal wound healing altogether?" That is unlikely for any initial keratorefractive procedure but the adjustable corneal annular segments of the present invention makes possible an adjustment that avoids the variable effects of corneal wound healing by minimally disturbing corneal tissue.

The essence of this invention lies in the assumption that individual responses to any kerato-refractive surgical procedures are variable, that even a "perfect" nomogram will not lead to a reliably predictable result in a particular individual, that a simple, safe, and effective technique for corneal curvature adjustment is necessary and that this modification should minimally disturb surrounding tissue thus allowing for a predictable effect. It should also be easily accomplished at some post-operative date after implantation of the device and after factors affecting corneal curvature changes have stabilized. A key feature of this invention lies in the ability of the device in its various embodiments to allow peripheral corneal volume displaced to be modified with ease at the time of implantation but more importantly on multiple occasions thereafter by simple removal of strand material from the implanted device, thus allowing fine-tuning of the refractive outcome.

In conclusion, in correcting refractive errors with this technique, the feeling of finality does not set in even with an initial inaccurate correction, with inadequate adjustment, or even when the last strand is removed because the device itself can be easily removed or better yet, left in place while other refractive procedures, such as laser ablation surgery are considered, if that point is ever reached.

It is also to be appreciated that the foregoing description of the invention has been presented for purposes of illustrations and explanation and is not intended to limit the invention to the precise form of apparatus and manner of practice herein. It is to be appreciated therefore, that changes may be made by those skilled in the art without departing from the spirit of the invention.

What is claimed is:

1. A corneal implant for placement into a human cornea for refractive correction comprising:

At least three ring-shaped flexible strands; and

At least two bands surrounding the strands to maintain the strands in relative close proximity to one another.

* * * * *

UNITED STATES PATENT AND TRADEMARK OFFICE
CERTIFICATE OF CORRECTION

PATENT NO. : 6,159,241
DATED : December 12, 2000
INVENTOR(S) : Joseph Y. Lee; Stephen I. Jang It is certified that error appears in the above-identified patent and that said Letters Patent is hereby corrected as shown below:

<u>Title page,</u>
Change the name of the assignee from "Joseph Y. Lee" to -- MicroOptix LLC --.

Signed and Sealed this

Twenty-fifth Day of September, 2001

Attest:

*Nicholas P. Godici*

NICHOLAS P. GODICI
*Attesting Officer*   *Acting Director of the United States Patent and Trademark Office*